United States Patent
Bates

(10) Patent No.: US 8,800,383 B2
(45) Date of Patent: Aug. 12, 2014

(54) FLOW MONITORED PARTICLE SENSOR

(75) Inventor: Thomas Bates, Westminster, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 174 days.

(21) Appl. No.: 13/392,057

(22) PCT Filed: Aug. 24, 2010

(86) PCT No.: PCT/US2010/046438
§ 371 (c)(1),
(2), (4) Date: Apr. 24, 2012

(87) PCT Pub. No.: WO2011/025763
PCT Pub. Date: Mar. 3, 2011

(65) Prior Publication Data
US 2012/0222495 A1    Sep. 6, 2012

Related U.S. Application Data

(60) Provisional application No. 61/236,318, filed on Aug. 24, 2009.

(51) Int. Cl.
*G01F 1/42* (2006.01)

(52) U.S. Cl.
USPC ...................................... 73/861.61

(58) Field of Classification Search
USPC ............. 73/53.01, 863.03; 250/338.5; 377/10
See application file for complete search history.

(56) References Cited

U.S. PATENT DOCUMENTS

| | | |
|---|---|---|
| 3,941,982 A | 3/1976 | Knollenberg et al. |
| 4,011,459 A | 3/1977 | Knollenberg et al. |
| 4,571,079 A | 2/1986 | Knollenberg |
| 4,594,715 A | 6/1986 | Knollenberg |
| 4,607,228 A | 8/1986 | Reif |

(Continued)

FOREIGN PATENT DOCUMENTS

| | | |
|---|---|---|
| JP | 56-039420 | 4/1981 |
| JP | 03-296622 | 12/1991 |

(Continued)

OTHER PUBLICATIONS

Freescale Semiconductor, Inc. (May 2012) "Technical Data Sheet: Freescale Semiconductor," Copyright 2006-2012. Rev. 5.1, Document No. MP3H6115A.

(Continued)

*Primary Examiner* — Jewel V Thompson
(74) *Attorney, Agent, or Firm* — Lathrop & Gage LLP

(57) ABSTRACT

Provided are devices and methods for monitoring flow rate in aerosol particle counters. The particle sensor has a particle counter, a flow measurement orifice comprising a differential pressure sensor for measuring differential pressure (DP) across the flow measurement orifice during particle sensor operation and a critical flow orifice. A vacuum source pulls ambient gas through each of the particle counter, flow measurement orifice and critical flow orifice. An atmospheric pressure sensor measures atmospheric pressure (AP) and a bench pressure sensor measures pressure in the particle sensor (BP). The output from the sensors is used to identify a flow condition, such as by a monitor operably connected to each of the differential pressure sensor, atmospheric pressure sensor and bench pressure sensor. In this manner, deviation in flow rate from a target flow rate is readily monitored without the need for expensive sensors or other flow-controlling components.

23 Claims, 4 Drawing Sheets

(56) References Cited

U.S. PATENT DOCUMENTS

| | | | |
|---|---|---|---|
| 4,636,075 | A | 1/1987 | Knollenberg |
| 4,728,190 | A | 3/1988 | Knollenberg |
| 4,740,988 | A | 4/1988 | Knollenberg et al. |
| 4,798,465 | A | 1/1989 | Knollenberg |
| 4,893,928 | A | 1/1990 | Knollenberg |
| 4,893,932 | A | 1/1990 | Knollenberg |
| 4,984,889 | A | 1/1991 | Sommer |
| 4,999,498 | A * | 3/1991 | Hunt et al. ............... 250/338.5 |
| 5,000,052 | A * | 3/1991 | Sipin ........................ 73/863.03 |
| 5,282,151 | A | 1/1994 | Knollenberg |
| 5,317,930 | A | 6/1994 | Wedding |
| 5,410,403 | A * | 4/1995 | Wells .......................... 356/335 |
| 5,467,189 | A | 11/1995 | Kreikbaum et al. |
| 5,493,123 | A | 2/1996 | Knollenberg et al. |
| 5,515,164 | A | 5/1996 | Kreikbaum et al. |
| 5,553,507 | A | 9/1996 | Basch et al. |
| 5,600,438 | A | 2/1997 | Kreikbaum et al. |
| 5,671,046 | A | 9/1997 | Knowlton |
| 5,751,422 | A | 5/1998 | Mitchell |
| 5,805,281 | A | 9/1998 | Knowlton |
| 5,825,487 | A | 10/1998 | Felbinger et al. |
| 5,861,950 | A | 1/1999 | Knowlton |
| 5,903,338 | A | 5/1999 | Mavliev et al. |
| 6,113,947 | A | 9/2000 | Cleland et al. |
| 6,167,107 | A * | 12/2000 | Bates ............................. 377/10 |
| 6,246,474 | B1 | 6/2001 | Cerni et al. |
| 6,275,290 | B1 | 8/2001 | Cerni et al. |
| 6,615,679 | B1 | 9/2003 | Knollenberg et al. |
| 6,709,311 | B2 | 3/2004 | Cerni |
| 6,859,277 | B2 | 2/2005 | Wagner et al. |
| 6,900,439 | B2 | 5/2005 | Komiyama et al. |
| 6,903,818 | B2 | 6/2005 | Cerni et al. |
| 6,945,090 | B2 | 9/2005 | Rodier |
| 7,030,980 | B1 | 4/2006 | Sehler et al. |
| 7,088,446 | B2 | 8/2006 | Cerni |
| 7,088,447 | B1 | 8/2006 | Bates et al. |
| 7,208,123 | B2 | 4/2007 | Knollenberg et al. |
| 7,235,214 | B2 | 6/2007 | Rodier et al. |
| RE39,783 | E | 8/2007 | Cerni et al. |
| 7,456,960 | B2 | 11/2008 | Cerni et al. |
| 7,576,857 | B2 | 8/2009 | Wagner |
| 7,667,839 | B2 | 2/2010 | Bates |
| 7,796,255 | B2 | 9/2010 | Miller |
| 7,916,293 | B2 | 3/2011 | Mitchell et al. |
| 7,973,929 | B2 | 7/2011 | Bates |
| 7,985,949 | B2 | 7/2011 | Rodier |
| 8,027,035 | B2 | 9/2011 | Mitchell et al. |
| 8,154,724 | B2 | 4/2012 | Mitchell et al. |
| 8,174,697 | B2 | 5/2012 | Mitchell et al. |
| 8,427,642 | B2 | 4/2013 | Mitchell et al. |
| 2005/0028593 | A1 | 2/2005 | Rodier |
| 2005/0100181 | A1 | 5/2005 | Croft et al. |
| 2007/0229825 | A1 | 10/2007 | Bates |
| 2009/0190128 | A1 | 7/2009 | Cerni et al. |
| 2009/0268202 | A1 | 10/2009 | Wagner |

FOREIGN PATENT DOCUMENTS

| | | |
|---|---|---|
| JP | 08-506901 | 7/1996 |
| JP | 2002-505671 | 2/2002 |
| WO | WO 99/22219 | 5/1999 |
| WO | WO 99/56106 | 11/1999 |
| WO | WO 01/06333 | 1/2001 |
| WO | WO 01/63250 | 8/2001 |
| WO | WO 2007/126681 | 11/2007 |
| WO | WO 2009/073649 | 6/2009 |
| WO | WO 2009/073652 | 6/2009 |
| WO | WO 2011/025763 | 3/2011 |

OTHER PUBLICATIONS

Freescale Semiconductor, Inc. (Sep. 2009) "Technical Data Sheet: Freescale Semiconductor," Copyright 2006-2009. Rev. 12, Document No. MPXV5004G.

International Search Report and Written Opinion Corresponding to International Application No. PCT/US2010/046438 mailed Oct. 19, 2010.

Office Action corresponding to Japanese Patent Application No. P2012-526897, dispatched Jan. 7, 2014.

Search Report corresponding to European Patent Application No. 10 812 542.8, dispatched Jan. 28, 2014.

* cited by examiner

FLOW MONITORED PARTICLE SENSOR

CROSS-REFERENCE TO RELATED APPLICATIONS

This application is the U.S. national stage application under 35 U.S.C. §371 of International Application No. PCT/US2010/046438, filed Aug. 24, 2010, which claims benefit of U.S. provisional patent application 61/236,318 filed Aug. 24, 2009, each of which is hereby incorporated by reference to the extent it is not inconsistent with the present disclosure.

BACKGROUND OF THE INVENTION

Aerosol optical particle sensors are important in a number of fields. For example, the micro-contamination industry is reliant on the use of aerosol optical particle sensors to provide a quantitative assessment of contamination. Aerosol optical particle sensors are employed for point of use measurement of air-born particle contamination in clean-rooms and clean zones. Generally, these particle sensors are low cost and do not rely on internal pumps to generate the required airflow through the sensor. The particle sensors instead rely on connection to house vacuum systems in order to generate flow. The flow rate is generally controlled by connecting the vacuum system to a low cost critical flow orifice located in the particle sensor. In order to accurately quantify the concentration of particles detected by the particle sensor, the flow-rate of the gas introduced to the sensor must be known. For example, an undetected flow-rate decrease of 15% would lead to a particle contamination concentration level determination that is 15% less than actual. Accordingly, it is important that the flow-rate of the gas being sampled by the sensor be either measured or accurately alarmed to provide the user with an indication that the flow-rate has deviated from a certain user-specified level.

A critical flow orifice to control volumetric flow rate is a well known technique to help ensure flow-rate is maintained. Critical flow orifices are well established in the art (see, e.g., Willeke/Baron, "Aerosol Measurement"; and Hinds, "Aerosol Technology"). Although a critical flow orifice is a very good low cost volumetric flow control device, such an orifice does not provide the capacity to monitor volumetric flow rate in a low cost and accurate manner. Off-the-shelf flow sensors can be utilized, but cost hundreds of dollars per particle sensor. Internal flow monitoring can be added to the particle sensor, such as described in U.S. Pat. No. 6,167,107, Air Pump for Particle Sensing Using Regenerative Fan, and Associated Methods, Jul. 16, 1999. Such internal flow-monitoring, however, also requires flow sensing devices that in total cost greater than one hundred dollars. Such costs make the use of such devices in low cost aerosol optical particle sensors impractical.

Accordingly, there is a need for an intelligent flow monitoring system that can accurately and reliably monitor flow rate in a particle sensor without significantly adding to the cost or complexity of the particle sensor. One object of the invention, therefore, is to provide devices and methods for monitoring flow rate in a particle sensor and identifying when the flow rate has deviated from a target flow rate so that appropriate remedial action may be taken.

SUMMARY OF THE INVENTION

Provided herein is a low-cost particle sensor with an accurate volumetric flow monitoring device that can reliably monitor the flow rate of sampled gas. In particular, the devices and methods provided herein are useful for identifying adverse flow events within the sensor that may otherwise remain undetected. The system presented herein provides flow monitoring in a particle sensor without the need for expensive flow or pressure sensors, and/or blowers for generating controlled flow-rates. Instead, flow may be reliably generated via a vacuum source, and flow-rate monitored as described herein.

Use of one differential pressure sensor and two absolute pressure sensors, along with algorithms based on the output of these sensors, facilitates the ability to produce a low-cost intelligent flow monitoring solution that is both accurate and inexpensive. The systems provide the capability of accurately assessing and identifying a flow condition error and, optionally, whether the flow condition error is related to a flow input obstruction ("upstream pressure loss") or a loss in vacuum ("downstream vacuum loss"). Conventional particle sensors, in contrast, even those capable of monitoring flow-rate, do not distinguish the reason for a flow rate condition error.

In one embodiment, provided is a method of monitoring volumetric flow rate of a gas in a particle sensor by providing a particle sensor. The particle sensor has a flow measurement orifice comprising a differential pressure sensor for measuring differential pressure across the flow measurement orifice, a critical orifice and a vacuum system for generating gas flow across the flow measurement orifice and the critical orifice. A flow of gas is generated through the particle sensor by establishing a vacuum pressure at a position downstream of the critical orifice. Although the sensor may detect particles suspended in any gas, in an embodiment the gas is air, such as air in a manufacturing facility or clean room. Pressure drop (DP) is determined across the flow measurement orifice, such as by differential pressure sensor. Atmospheric pressure (AP) and pressure in the particle sensor (BP) at a position that is upstream of the critical orifice are determined. The DP, AP and BP values are used to identify a flow condition, thereby monitoring the flow rate in the particle counter.

In an aspect, the flow condition is selected from the group consisting of a satisfactory flow rate and a flow rate error condition. In another aspect, the flow condition is a flow rate error condition.

In an aspect, any of the methods provided herein further relate to identifying a flow rate error condition as a vacuum-induced flow loss or an inlet-induced flow loss.

In an embodiment, the invention provides algorithms for identifying a flow rate error condition. For example, a vacuum-induced flow loss can be identified for:

$$DPI_{corr} < (1-\text{TOLERANCE})^2 * DPI_{target}; \text{ or}$$

$$DPI_{corr} > (1+\text{TOLERANCE})^2 * DPI_{target};$$

wherein:
$DPI_{corr}$ is the differential pressure sensor current reading across the flow measurement orifice during particle sensor operation;
TOLERANCE is a user-selected flow rate tolerance level;
$DPI_{target}$ is a differential pressure sensor target value calculated as:

$$DPC_{corr}/BPI_{corr}/BPC_{cor}), \text{ wherein:}$$

$DPC_{corr}$ is the differential pressure sensor value during system calibration;
$BPI_{corr}$ is the bench pressure value during particle sensor operation; and
$BPC_{corr}$ is the bench pressure value during system calibration.

In another embodiment, the method is for identifying an inlet-induced flow loss, wherein the error is identified for:

$$APR_{insitu} < (1-TOLERANCE)*APR_{calibration}; \text{ or}$$

$$APR_{insitu} > (1+TOLERANCE)*APR_{calibration};$$

wherein:
$APR_{insitu}$ is the pressure ratio of $API_{corr}$ and $BPI_{corr}$ during particle sensor operation: $(BPI_{corr}/API_{corr})$;
$API_{corr}$ is the atmospheric pressure value during particle sensor operation;
$BPI_{corr}$ is the bench pressure value during particle sensor operation;
TOLERANCE is a user-selected flow rate tolerance level;
$APR_{calibration}$ is the pressure ratio of $APC_{corr}$ and $BPC_{corr}$: $(BPC_{corr}/APC_{corr})$, wherein:
$BPC_{corr}$ is the bench pressure value at calibration; and
$APC_{corr}$ is the atmospheric pressure at calibration.

In an embodiment, the TOLERANCE value is selected from a range that is greater than or equal to 5% and less than or equal to 15%, such as a value that is 10%. The lower limit of TOLERANCE values is governed by the accuracy of the sensors. In particular, a differential pressure sensor that is not capable of reliably detecting a change in pressure drop less than 10% effectively results in a floor in the TOLERANCE value of 10%. In contrast, a differential pressure sensor capable of detecting changes in pressure drop of 10% may be used reliably for any TOLERANCE value that is greater than or equal to 10%.

In an aspect, BPI is measured within an optical block of the particle sensor. In an aspect, the flow measurement orifice is positioned upstream of the critical orifice. In an aspect, the vacuum source is a house vacuum. In an aspect, the gas is air.

Any of the methods described herein may be used to identify a flow condition that is a monitored flow-rate that deviates by 10% or more from a target flow rate. In an aspect, the target flow rate is a volumetric flow rate of gas, such as a target flow rate of 1 CFM (cubic feet per minute).

In another embodiment, any of the methods further comprise identifying a source of said flow condition deviation, wherein the source is a vacuum-induced loss or an inlet-induced flow loss.

Also provided herein are devices, such as particle sensors for detecting and counting particles in a gas. In an aspect, the invention is a particle sensor comprising a particle counter, a flow measurement orifice comprising a differential pressure sensor for measuring differential pressure across the flow measurement orifice (DPI) during particle sensor operation, a critical flow orifice, a vacuum source for pulling ambient gas through each of the particle counter, flow measurement orifice and critical flow orifice, an atmospheric pressure sensor for measuring atmospheric pressure (API), a bench pressure sensor for measuring pressure in the particle sensor (BPI), and a monitor operably connected to each of the differential pressure sensor, atmospheric pressure sensor and bench pressure sensor, wherein the monitor identifies a flow condition from DPI, API and BPI.

"Monitor" refers to any component or compilation of components known in the art that provides a detectable signal that identifies one or more flow conditions. For example, the monitor can be an alarm that generates a signal to indicate when the flow condition is a flow-rate error. Alternatively, the monitor may simply provide a numerical read-out that a user may examine to determine the flow condition in the sensor.

In an aspect, the particle sensor indicates a flow-rate error that is a 10% or greater deviation from a target flow rate of gas through the particle sensor.

In another aspect, the particle sensor indicates a flow-rate error for one or more conditions defined by:

$$DPI_{corr} < (1-TOLERANCE)^2 * DPI_{target};$$

$$DPI_{corr} > (1+TOLERANCE)^2 * DPI_{target};$$

$$APR_{insitu} < (1-TOLERANCE)*APR_{calibration}; \text{ and}$$

$$APR_{insitu} > (1+TOLERANCE)*APR_{calibration};$$

wherein:
$DPI_{corr}$ is the differential pressure sensor current reading across said flow measurement orifice during particle sensor operation;
TOLERANCE is a user-selected flow rate tolerance level;
$DPI_{target}$ is a differential pressure sensor target value calculated as:

$$DPC_{corr} * (BPI_{corr}/BPC_{corr}), \text{ wherein:}$$

$DPC_{corr}$ is the differential pressure sensor value during system calibration;
$BPI_{corr}$ is the bench pressure value during particle sensor operation; and
$BPC_{corr}$ is the bench pressure value during system calibration.
$APR_{insitu}$ is the pressure ratio of $API_{corr}$ and $BPI_{corr}$ during particle sensor operation: $(BPI_{corr}/API_{corr})$;
$API_{corr}$ is the atmospheric pressure value during particle sensor operation;
$BPI_{corr}$ is the bench pressure value during particle sensor operation;
$APR_{calibration}$ is the pressure ratio of $APC_{corr}$ and $BPC_{corr}$: $(BPC_{corr}/APC_{corr})$, wherein:
$APC_{corr}$ is the atmospheric pressure at calibration.

In another aspect, the particle sensor identifies a flow condition that is a satisfactory flow condition, wherein the satisfactory flow condition is a flow-rate that is less than or equal to 10% deviation from a target flow-rate. The identification of a satisfactory flow condition may correspond to ongoing sampling by the particle sensor.

In an embodiment, the flow measurement orifice is positioned between the particle counter and critical flow orifice. In another embodiment, the bench pressure sensor measures pressure within an optical block of the particle counter.

In another aspect, the invention relates to sensors that are each of low-cost, thereby ensuring the particle sensor in which the sensors are incorporated remains low cost. Low cost can be defined in any number of manners ranging from functional or performance-based parameters or in terms of absolute cost. For example, a sensor that is low cost may reflect that the sensor's sensitivity, repeatability or accuracy to detect changes in pressure. For example, certain low cost sensors have a maximum accuracy of 2.5% (full scale span), whereas higher cost sensors are generally of higher sensitivity, repeatability and accuracy. Alternatively, low cost may be expressed in terms of the cost, as provided herein, of the sensors used in the particle sensor.

Without wishing to be bound by any particular theory, there can be discussion herein of beliefs or understandings of underlying principles or mechanisms relating to embodiments of the invention. It is recognized that regardless of the ultimate correctness of any explanation or hypothesis, an embodiment of the invention can nonetheless be operative and useful.

DETAILED DESCRIPTION OF THE INVENTION

Figure 1:
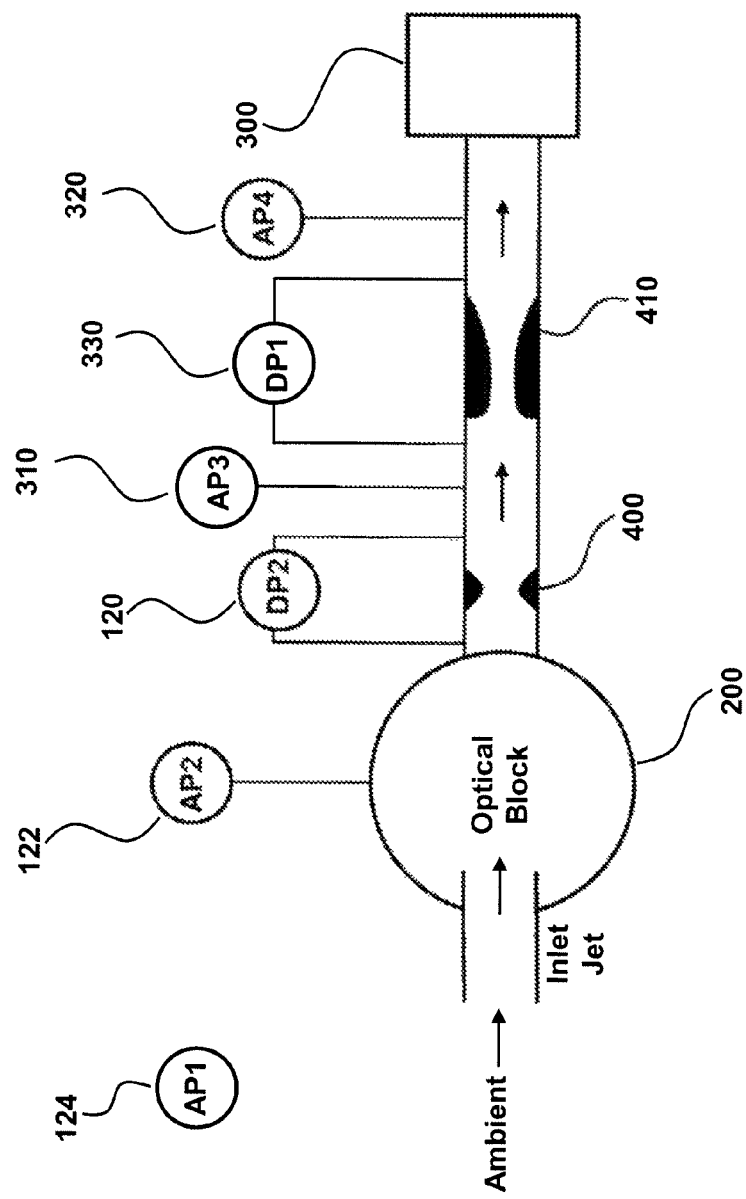
FIG. 1 is a schematic of a particle sensor summarizing relevant pressure sensors and locations thereof.

The following patents provide useful background relating to particle sensors and airflow systems: U.S. Pat. Nos. 5,467,189; 5,515,164; 5,600,438; 4,571,079; 4,984,889; 4,594,715; 5,825,487; and U.S. Pat. No. 6,167,107. Each of the aforementioned patents is incorporated herein by reference to the extent not inconsistent with the present disclosure.

"Flow condition" refers to the flow status of the gas that is being drawn through the particle sensor. In an aspect, flow condition is based on a comparison of a monitored flow rate and target flow rate. Target flow rate refers to a flow rate the particle sensor is calibrated to use and generally depends on the characteristics of the critical flow orifice. In an aspect, the critical flow orifice is sized to provide a target flow rate that is fixed at a desired value. Although the devices and methods provided herein are compatible for any desired target flow rate, in an embodiment the target flow rate is 1 CFM. A tolerance level (relative to the target flow rate) is selected so that the particle sensor continues to operate normally so long as the monitored flow rate is within the selected tolerance level. This is referred to as a "satisfactory flow condition." If, however, the flow monitoring reveals the flow rate is outside the tolerance level, the particle sensor is capable of indicating a "flow rate error condition." In addition, a "flow rate warning condition" may correspond to a monitored flow rate that is approaching the tolerance level, but has not yet exceeded the tolerance level.

The devices and methods provided herein are also capable of distinguishing the source of the flow rate error condition. "Vacuum-induced flow loss" refers to an event at the downstream end of the particle sensor and involves the vacuum source, such as a malfunction in the vacuum source, or a leak in the particle sensor and/or vacuum source connection, thereby leading to vacuum loss. In contrast, an "inlet-induced flow loss" refers to an obstruction or other event located in the upstream end of the particle sensor, such as toward or at the inlet orifice or inlet tube, that causes an increase in the pressure drop at a location upstream from the critical flow orifice.

"TOLERANCE" is a user-selected or manufacturer-selected value and can be expressed in terms of a percentage relative to the target flow rate. For example, if TOLERANCE is selected to be 10%, the device and related methodology will identify a flow condition error if the monitored flow rate deviates by 10% or more from the target flow rate (e.g., greater than 110% of target flow rate or less then or equal to 90% of target flow rate). TOLERANCE may be expressed as a percentage or as a corresponding numerical value.

In an aspect, the total cost of the sensors for this system (at present levels) is less than $25 when purchased in quantities as low as 1000 pieces. This ensures that the resultant particle sensor having intelligent flow monitoring is also low cost. The differential pressure sensor is any pressure sensor of sufficient accuracy to detect a desired pressure difference. For example, in situations where it is desired to reliably and accurately detect a 10% change (e.g., TOLERANCE=10%), a suitable differential pressure sensor is a Freescale® Semiconductor MPXV5004DP differential pressure sensor and suitable absolute pressure sensors include a Freescale® Semiconductor MP3H6115A.

"Operably connected" refers to a configuration of elements such as a monitor and sensors, wherein an action or reaction of one element affects another element, but in a manner that preserves each element's functionality. For example, the action of a sensor (corresponding to, for example, a voltage output from a pressure transducer) may be used to determine one or more variables that are processed to identify a flow condition, and specifically flow rate error, thereby resulting in the monitor generating a signal to warn the user of the flow condition error. In this example, the monitor is said to be operably connected to the sensor(s).

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, the scope of the invention should be determined by the appended claims and their equivalents, rather than by the examples given.

Example 1

Critical Flow Orifice for Controlling Flow-Rate

The required critical pressure drop needed is given by the following equation.

$$P_v/P_a = [2/(k+1)]^{k/(k-1)} \quad (1)$$

$P_v$=Pressure on vacuum side of critical flow orifice
$P_a$=Pressure on upstream side of critical flow orifice
k=Gas specific heat ratio=7/5 for diatomic gases=1.4
Substituting 1.4 for k yields the simplified equation:

$$P_v/P_a = 0.53 \quad (2)$$

At standard conditions $P_a$=14.7 psi. Therefore, the required critical pressure drop at standard conditions is 7.791 psi (15.9" Hg).

At standard conditions a critical flow orifice will maintain constant volumetric flow when the downstream vacuum level is greater than 15.9" Hg. Under these conditions the velocity in the throat of the orifice is the speed of sound, and a further increase in the downstream vacuum level does not increase the velocity through the throat. Most prior art particle sensors utilize a knife-edge critical flow orifice. This requires the user to provide a vacuum pumping system that can maintain a minimum of 15.9" Hg vacuum level at the particle sensor's specified flow rate.

There are two specific conditions that can cause an error in flow rate with a critical orifice particle sensor. One failure condition is if the vacuum level falls below the vacuum level required to maintain critical flow. This can happen, for example, if the house vacuum system loses capacity or if there is a disturbance between the house system and the vacuum connection to the particle sensor. The second failure condition is if there is a change in inlet pressure drop to the particle sensor. This can be caused, for example, by an obstruction in the particle sensor inlet.

Example 2

Low-Cost Flow Monitoring

FIG. 1 details the fluidic design features of a particle sensor that may be used to intelligently monitor flow rate. The particle sensor includes an inlet jet from which ambient air is drawn from the ambient environment into the optical block 200 of the particle sensor. The optical block is the portion of the system that performs the particle detection, as particles suspended in the moving air are drawn through a laser beam and scatter light energy before exiting the optical block.

The air is drawn through a flow measurement orifice 400. The differential pressure 120 across this orifice is used to measure the flow rate through the particle sensor. This differential pressure is minimized as its pressure drop is added directly to the required pressure drop of the critical flow orifice. The air is then drawn through a venturi critical flow orifice 410 before being pulled out of the sensor by the external vacuum system 300. The critical flow orifice is used to control the target flow rate of the particle sensor. The external vacuum source 300 provides the required force to draw air into the particle sensor.

Several important air pressure points are also detailed in FIG. 1. AP1 124 is the absolute air pressure of the ambient environment. AP2 122 is the absolute air pressure (referred herein as "bench pressure", BP) in the particle sensor and, in this example, of the optical block 200. Sensor 122 may be positioned anywhere along the particle sensor system so long as the pressure in the system is reliably measured. In one aspect, BP is measured at a position that is upstream of the critical orifice 410. In another aspect, BP is measured at a position that is upstream of the flow measurement orifice 400. DP2 120 is the differential pressure across the flow measurement orifice 400 and is used as an indication of flow-rate through the sensor. AP3 310 is the absolute air pressure of the critical flow orifice inlet. AP4 320 is the absolute air pressure of the applied vacuum system. DP1 330 is the differential pressure across the critical flow orifice.

The system will maintain a constant volumetric flow rate as determined by the cross-sectional area of the critical flow orifice, dependent on the ability of the vacuum source 300 to supply and maintain a minimum required level of vacuum. This orifice can be sized at the time of calibration to achieve the desired target volumetric flow rate of air drawn from the ambient environment (AP1). Accordingly, the ability to monitor AP1, as well as the other pressure point monitoring AP2, ensures that variation in AP1 (such as by change in altitude or in weather) are taken into account to ensure target volumetric flow rate is maintained. The volumetric flow rate into the system will remain constant as long as the vacuum level AP4 320 generated by the external vacuum source 300 is kept strong enough to produce the required differential pressure (330) across the critical flow orifice 410 to produce critical flow, and there is no change in the upstream pressure drop (e.g., 124 and 122: AP1–AP2; or 124 and 310: AP1–AP3).

The differential pressure 120 across flow measurement orifice 400 (e.g., DP2) will also remain constant as long as the flow rate remains constant. This makes DP2 an excellent choice for monitoring flow status of the system, as any changes in DP2 indicates the potential of a corresponding change in flow rate.

If the particle sensor is calibrated at one sight location and then moved to another it could be exposed to a significant change in ambient air pressure (124). Absolute air pressure varies depending on altitude, such as from sea level (407 inches of water) to a much lower level (338 inches of water) at an elevation of 5000 feet. This 17% change in ambient air pressure (AP) will not cause a significant change in the volumetric flow rate drawn into the particle sensor. The critical flow orifice pressure drop is limited by sonic air velocity, and sonic air velocity changes very little with elevations ranging, for example, from sea level to 5000 feet.

A change in elevation will cause a significant change in differential pressure (DP2) across the flow measurement orifice. Under the flow conditions encountered during normal particle sensor operation, the relationship between a change in differential pressure and volumetric flow rate can be expressed using the Bernoulli equation:

$$Q = K \cdot [(2 \cdot \Delta P)/\rho]^{1/2} \quad (3)$$

Q=Volumetric flow rate
K=empirically derived constant
ρ=Density

In this case, the change in ΔP is due to the change in absolute air pressure (and corresponding change in the air density, ρ, as reflected in the Ideal Gas Law shown below in Equation (4)). A 17% decrease in ambient air pressure will cause a 17% decrease in the differential pressure (DP2) across the flow measurement orifice. If (DP2) is used to generate a flow status indication for the particle sensor it must be capable of compensating for changes in ambient air pressure. This can be accomplished with the use of a low-cost (e.g., on the order of eight dollars) absolute air pressure sensor. This type of sensor has 1.5% repeatability and can be used to reliably detect a change in volumetric flow-rate that is 10% or greater than a target flow-rate.

There are two possible conditions that can cause flow error with a critical flow orifice particle sensor. The first condition is if the vacuum level 320 (AP4) falls below the vacuum level required to maintain critical flow. This can occur, for example, where there is a failure in the vacuum source 300 or a leak between the vacuum source and the particle sensor. When this condition happens, the critical flow orifice 410 begins to draw less ambient air flow into the particle sensor. The effect on the flow measurement orifice 120 (DP1) is determined from the Bernoulli equation, where from Equation (3) a change in pressure drop 120 across the flow measurement orifice 400 will decrease by the square of the flow rate. In other words, a 10% decrease in volumetric flow-rate will create a 19% drop in the measured differential pressure (120).

This relation between change in pressure drop and flow rate is advantageous as the accuracy requirements of the differential pressure sensor to detect a change in flow rate are lessened. For example, a particle sensor having a requirement that a 10% loss in flow is detected requires a differential pressure sensor 120 that must reliably detect a 19% change in pressure. Such a requirement can be satisfied with a low-cost differential pressure sensor (e.g., having a present cost of as little as ten dollars), and does not require a more expensive pressure sensor or other expensive devices that regulate flow rate, such as a regenerative blower. Accordingly, in an aspect any of the particle sensors described do not have any flow-regulating devices such as blowers or other components that regulate flow-rate.

Figure 3:
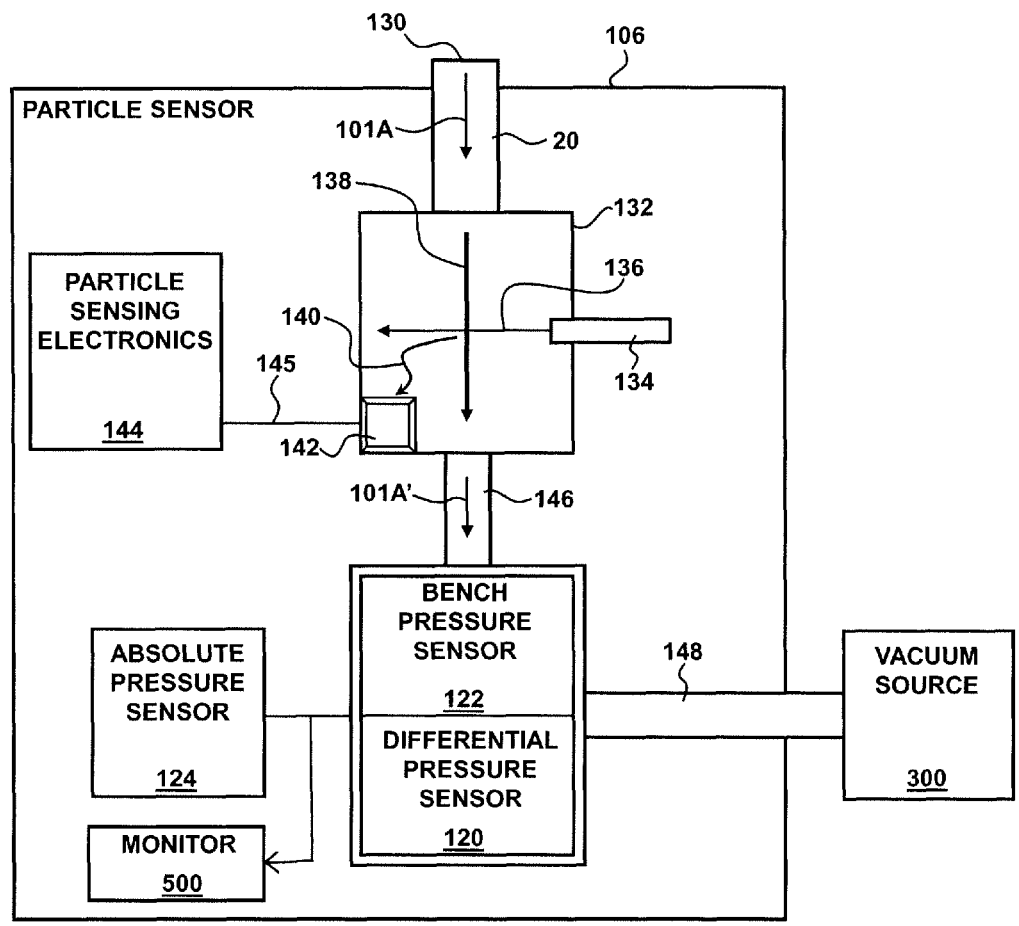
FIG. 3 illustrates additional detail of the particle sensor and airflow.

The other condition that can cause flow error in a critical flow orifice particle sensor is a change in inlet pressure drop such as caused by an obstruction in the particle sensor inlet. Referring to FIG. 3, this could arise from an obstruction in the airflow inlet tube 20 or in the inlet orifice 130, for example The flow rate loss caused by this situation can also be predicted from the Bernoulli equation (3) and Ideal Gas Law (4).

$$\text{Ideal Gas Law: } \rho = PM/RT \quad (4)$$

ρ=Density (kg/m3)
P=pressure (kPa)
M=Molar mass of air (28.97 kg/kmol)
R=Universal Gas Constant (8.314 kJ/kmol·K
T=Temperature (° K)

An obstruction in the inlet jet will cause an increase in the differential pressure drop across the inlet jet, and a resultant decrease in AP2 122 (BP) measured in the optical block 200 as shown in FIG. 1. Accordingly, the critical orifice inlet pressure 310 (AP3) becomes more negative in relation to the ambient environment 124 (API).

The critical flow orifice will continue to maintain the volumetric flow rate of its inlet pressure 310 (AP3). However, this is no longer the same volumetric flow rate drawn from the ambient environment. The loss of flow drawn into the system is a linear relationship. A 10% drop in inlet flow is associated with a 10% differential pressure difference between API or AP2 and AP3.

The effect on the flow measurement orifice is also predictable. The sensor 120 (DP) associated with flow measurement orifice 400 is exposed to a 10% drop in absolute air pressure, with no drop in volumetric flow as referenced to the absolute air pressure the orifice sits at. This is no different than the measurement error induced by a change in elevation. There is a linear relationship between absolute air pressure AP2 (BP) 122 and the differential pressure (DP1) 120 across the orifice 400. If the inlet flow decreases by 10%, the absolute pressure at AP2 (BP) 122 decreases by 10%, and the differential pressure 120 across the flow measurement orifice (DP2) decreases by 10%.

Such detection is much more difficult to detect than flow loss caused by system vacuum loss (where a pressure change as large as 19% may be used to detect 10% loss in flow). A differential pressure sensor 120 used to detect a 10% loss in flow, must be capable of reliably detecting a 10% loss in pressure. This forces the use of a highly repeatable, accurate and sensitive sensor that typically costs greater than ten times the cost of the low cost differential pressure sensor.

Figure 2:
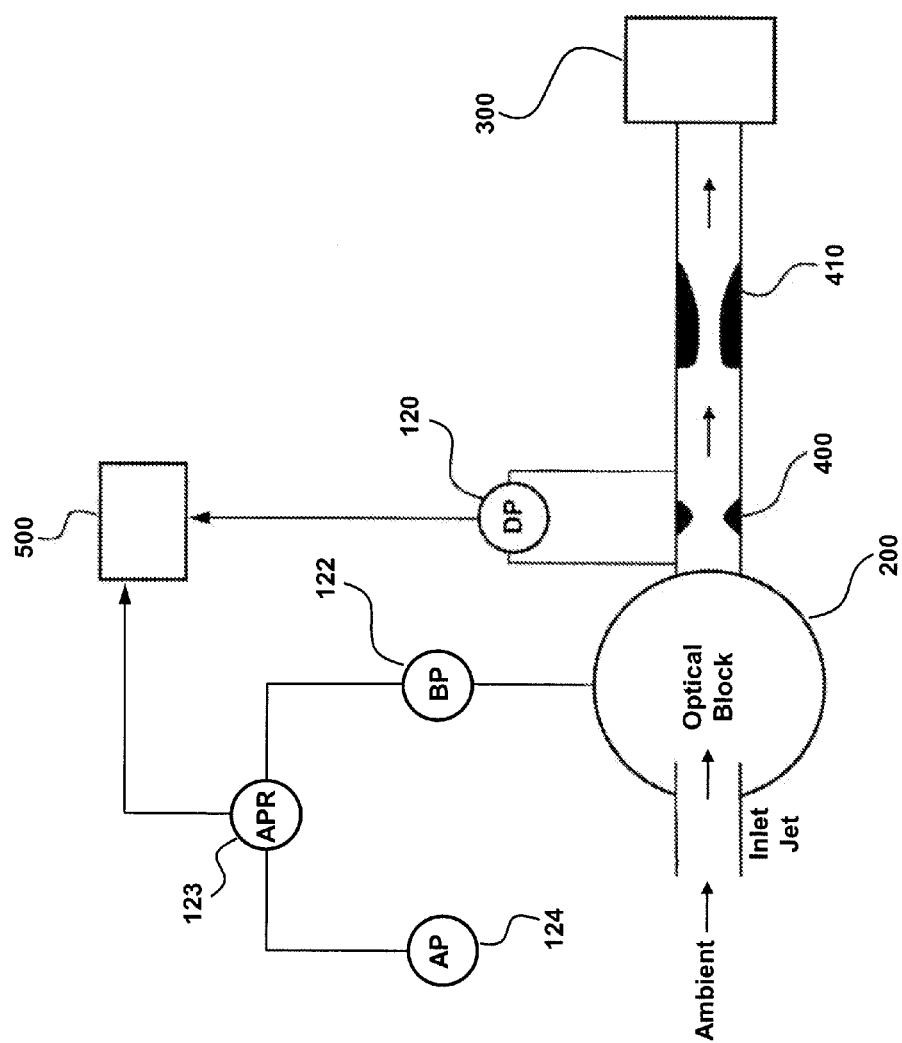
FIG. 2 is a schematic of a particle sensor showing relevant parameters that are measured or calculated in order to monitor flow condition in the particle sensor.

Referring to FIG. 2, the need for high-cost sensors or other flow-controlling devices, is avoided by using two low-cost absolute pressure sensors (124 and 122) to measure: the ambient air pressure (AP) surrounding the particle sensor; and bench pressure 122 (BP) and one low cost differential pressure sensor 120 that monitors pressure drop (and, therefore, flow rate) across flow measurement orifice 400. Each of sensors 120, 122, and 124 is used by monitor 500 and associated electronics that process the output of the sensors as described herein, to identify a flow condition of the gas that is introduced to the particle sensor (e.g., satisfactory, warning, error).

A 10% loss in ambient air flow caused by inlet restriction can only be created by a 10% pressure delta between the ambient environment (124) and the critical orifice inlet pressure (310). At sea level air pressure (407 inches of water absolute air pressure), this 10% difference would be 40.7 inches of water. This falls well within the accuracy specifications of available low cost absolute pressure sensors that typically have a maximum sensitivity or accuracy of 1.5% (6.9 inches of water).

Example 3

Algorithm for Identifying Flow Condition

Provided is a device and method for monitoring volumetric flow rate in a particle sensor by the use of one low cost differential pressure sensor and two low cost absolute pressure sensors. The focus of this method is to produce a low cost intelligent flow monitoring solution that is both better than 10% accurate (e.g., capable of reliably detecting a 10% or greater deviation from a target flow rate) and inexpensive.

One example of a suitable differential pressure sensor 120 is a Freescale® Semiconductor MPXV5004DP. This sensor has an accuracy specification of +/−2.5% full scale, through a temperature range of +/−5° C. from calibration temperature. The flow measurement orifice in the particle sensor can be sized to operate the differential pressure sensor at near full scale.

Since the accuracy is not specified beyond a temperature range exceeding +/−5° C. C, the additional error will need to be empirically derived. A reasonable temperature range for a particle sensor would be +/−15° C. Initial testing has indicated that an extension of the temperature range to +/−15° C. from the calibration point may increase the error to +/−7.5% full scale.

One example of a suitable absolute pressure sensor 122 and/or 124 is a Freescale® Semiconductor MP3H6115A. This sensor has an accuracy specification of +/−1.5% full scale (115 KPa), through a temperature range of 0 to 85° C. At sea level air pressure (101.325 KPa), this would correlate to 1.7% of measured air pressure.

A diagram of this intelligent flow monitoring system is provided in FIG. 2. AP 124 represents the absolute pressure sensor that is monitoring the atmospheric pressure of the ambient air environment. BP 122 represents the absolute pressure sensor that is monitoring the internal optical bench pressure of the particle sensor. DP 120 represents the differential pressure sensor monitoring the differential pressure across the flow measurement orifice. APR 123 represents the ratio of the internal optical bench pressure to the ambient environment pressure. A monitor 500 provides an indication of flow condition to a user. Referring to FIG. 2 the monitor is operably connected to differential pressure sensor 120 (DP), atmospheric pressure sensor 124 (AP) and bench pressure sensor 122 (BP). In accordance with the relationships between the various parameters obtained from sensors 120, 122, and 124 (see, e.g., Equations (5)-(12)), the monitor identifies a flow condition to the user, such as a satisfactory flow condition (flow is within tolerance range) or a flow error (flow is outside tolerance range). The monitor may simply alarm (visual and/or auditory) to signify a flow condition error. Optionally, the monitor may automatically turn off the particle sensor 106, such as by powering off the system or stopping gas flow.

A summary of the variable nomenclature and their description is provided in Table 1. Table 1 also provides detail related to when the variable is measured, such as during calibration or during sensor operation. Calibration can occur under no flow conditions or during a calibrated (e.g., known) flow. In-situ refers to a measurement during particle sensor operation. "Raw" refers to the base output value from the sensor, and is used along with the offset reading to calculate a "corrected" value for the parameter, as summarized in Table 1.

The system is capable of identifying a flow condition error associated with loss of vacuum under the following conditions:

$$DPI_{corr} < (1-\text{TOLERANCE})^2 * DPI_{target}; \quad (5) \text{ or}$$

$$DPI_{corr} > (1+\text{TOLERANCE})^2 * DPI_{target}; \quad (6)$$

In a system wherein TOLERANCE=10%=0.1 (e.g., identification of a flow condition error for a +/−10% deviation from target flow rate, and caused by a vacuum-induced flow loss or vacuum loss), Equations (5) and (6) become, respectively:

$$DPI_{corrected} < 0.81 * DPI_{target} \quad (7); \text{ or}$$

$$DPI_{corrected} > 1.21 * DPI_{target} \quad (8)$$

As discussed, flow error or failure arising from loss of vacuum is actually the easier of the two potential flow failures to detect. A loss of flow caused by vacuum loss will produce a differential pressure loss that has a squared function with respect to flow-rate. That is, a 10% change in flow will produce approximately a 20% change in differential pressure. The MPXV5004DP pressure sensor has +/−7.5% accuracy, and must reliably detect only a 20% change in pressure in order to reliably identify a 10% change in flow-rate. The error band of the pressure sensor accuracy is approximately 37.5% of the required system accuracy. This low cost differential pressure sensor can be reliably used to detect 10% flow change caused by vacuum system change.

The case of flow loss caused by an inlet restriction to the particle sensor is more difficult to detect. A particle sensor with a critical flow orifice connected to a large house vacuum system is considerably different than a portable particle counter with a small internal blower or pump.

U.S. Pat. No. 6,167,107, Air Pump for Particle Sensing Using Regenerative Fan, And Associated Methods, Jul. 16, 1999, describes a portable particle counter. The regenerative blower in those systems are generally only capable of producing a maximum vacuum level of approximately 20 inches of water. In addition, the blower flow rate will fall off as the inlet is restricted and the vacuum level increases to the maximum it is capable of producing. The blower reaches the maximum vacuum level at the same point that the system flow rate collapses to zero.

Those portable particle counters will have a complete collapse of flow rate if exposed to an inlet restriction that produces a differential pressure drop of more than 20 inches of water. At sea level air pressure of 407.8 inches of water (one atmosphere), a 20 inch of water differential pressure drop corresponds to a 4.9% drop from ambient air pressure. Therefore an inlet restriction of 20 inches of water can only cause a 4.9% drop in flow rate before the flow begins to collapse due to the blowers inability to produce sufficient vacuum. Once the flow collapses due to this issue, the change in differential pressure across the differential pressure sensor will respond similarly to the case of flow loss caused by vacuum loss to the system.

In the case of a particle sensor connected to a house vacuum system, the house vacuum system can produce an extremely large vacuum level. Typical house vacuum systems produce vacuum levels that are greater than or equal to 244.7 inches of water (18 inches of mercury). The minimal amount of vacuum level required to reach critical flow with a critical flow orifice of the exemplified system at sea level air pressure is 216.2 inches of water (15.9 inches of mercury). Therefore, the house system must produce at least a minimum vacuum level of 216.2 inches of water.

A particle sensor running on a house vacuum system can be exposed to a significant inlet restriction before the system flow rate drops due to the vacuum level collapsing. A 40.7 inch of water differential pressure inlet restriction will produce a 10% flow loss at sea level air pressure of 407.8 inches of water. Flow loss due to loss of vacuum will not happen as long as the house vacuum level is at least 40.7 inches of water greater than the minimal vacuum requirement of the critical flow orifice (216.2 inches of water).

In this scenario, the differential pressure across the flow measurement orifice does not have a squared relationship to flow loss as in the case of flow loss due to vacuum loss. Rather, the differential pressure has a linear relationship with flow loss. This is the same relationship that exists when the flow measurement orifice is exposed to changes in elevation.

The critical flow orifice will continue to draw the appropriate volumetric flow rate, but it is now referenced to the optical bench air pressure 122 (BP), not the ambient air pressure 124 (AP) outside of the optical bench. The volumetric flow rate drawn from the ambient environment will be decreased by the ratio of the optical bench and ambient pressures 123 (APR). The flow measurement orifice 400 will produce a lower differential pressure 120 that is also decreased by the ratio 123 of the optical bench 122 and ambient 124 pressures. A 10% flow loss from the ambient environment will produce a 10% drop in differential pressure 120.

A 10% change in flow caused by inlet restriction will produce a 10% change in differential pressure. The MPXV5004DP pressure sensor has +/−7.5% accuracy, and must now reliably detect only a 10% change in pressure. The error band of the pressure sensor accuracy is now approximately 75% of the required system accuracy. This low cost differential pressure sensor cannot be reliably used to detect 10% flow change caused by inlet restriction.

Since the change in flow rate is caused by a change in the ratio of the optical bench air pressure and ambient air pressure, this ratio can instead be used to predict flow loss induced by inlet restriction.

In this example, we use absolute pressure sensors that are the Freescale® Semiconductor MP3H6115A. This sensor has an accuracy specification of +/−1.5% full scale (115 KPa), through a temperature range of 0 to 85° C. At sea level air pressure (101.325 KPa), this would correlate to 1.7% of measured air pressure. In this application, two pressure sensor measurements are required. An industry standard would be to add the 1.7% accuracy specifications in quadrature: $(1.7^2 + 1.7^2)^{1/2} = 2.4 = 2.4\%$.

An inlet restriction that causes a 10% change in flow will produce a 10% change in differential pressure (DP). The two MP3H6115A pressure sensors have a combined accuracy of 2.4%, and must reliably detect a 10% change in pressure. The error band of the pressure sensor accuracy is now approximately 24% of the required system accuracy. These low cost absolute pressure sensors can be reliably used to detect 10% flow change caused by inlet restriction.

The pass/fail criteria for a user defined tolerance level caused by inlet restriction is, a flow condition that is a flow rate failure if there is a greater than TOLERANCE level deviation from a target flow rate for:

$$APR_{insitu} < APR_{calibration} \times (1-\text{TOLERANCE}) \quad (9) \text{ or}$$

$$APR_{insitu} > APR_{calibration} \times (1+\text{TOLERANCE}) \quad (10)$$

The pass/fail criteria for a TOLERANCE of 10% flow change caused by inlet restriction is identified as a flow condition error (e.g., greater than 10% flow-rate deviation) if:

$$APR_{insitu} < APR_{calibration} \times 0.9 \quad (11) \text{ or}$$

$$APR_{insitu} > APR_{calibration} \times 1.1 \quad (12)$$

Because the system compensates for the absolute air pressure of the flow measurement orifice (in this example, the same as the optical bench), the system maintains accuracy at various elevations. In this manner, the system can be calibrated at one altitude (e.g., by the manufacturer), and will remain in calibration when shipped to another location (e.g., to the customer) at a different altitude. The system also compensates for changes in local air pressure due to weather. The compensation for absolute air pressure is addressed by the following portion of the flow monitoring algorithm:

$$DP_{target} = DPC_{corrected} \times (BPI_{corrected}/BPC_{corrected}) \quad (13)$$

The system will compensate for changes in local air pressure and changes in elevation. The system will detect 10% flow loss, induced by vacuum loss, by monitoring for a 19% drop in differential pressure (DP). The system will detect 10% flow loss, induced by inlet restriction, by monitoring for a 10% drop in differential pressure between (AP) and (BP). In this manner, low cost DP (120), AP (124) and BP (122) sensors may be used to reliably detect flow losses as low as 10%. Each of these pressure sensors may be purchased at a sufficiently low-cost so that the resultant particle sensor remains low cost, but provides intelligent flow monitoring without substantially adding to the particle sensor's cost.

FIG. 3 illustrates further detail of particle sensor 106 and the associated airflow mechanics, including vacuum source 300, that draws air into particle sensor 106. FIG. 3 also illustrates positioning of sensors 120, 122, 124 used by particle sensor 106 to monitor volumetric flow-rate. In particular, output (such as output and subsequent algorithm processing as provided herein) from sensor 120, 122, and 124 is directed to monitor 500 where flow condition is provided to a user. Vacuum source 300 draws air 101A into particle sensor 106 through inlet orifice 130, connected for fluid communication with a downstream tube 146, and particle counter 132 (e.g., optical block 200) to evaluate particulates within a flow 138 of air 101A. Particle sensor 106 preferably includes an airflow tube 20, to create flow 138. As known in the art, a laser 134 generates a laser beam 136 that illuminates flow 138 such that scattered energy 140, indicative of particles in flow 138, is detected by detector 142. Particle sensing electronics 144 evaluate signals from detector 142, through signal line 145, to quantify these particulates for a selected target volumetric flow rate, e.g., 1 CFM.

Vacuum source 300 further draws air 101A' from counter 132 through connecting tube 146 and through airflow and internal atmospheric sensors 120, 122. Airflow sensor 120 measures airflow of air 101A' across a restriction (e.g., flow measurement orifice 400), described in connection with FIG. 4, and internal atmospheric sensor (e.g., bench pressure sensor) 122 measures pressure within sensor 106. In one aspect, sensor 122 measures pressure in optical block 200 (corresponding to counter 132). Vacuum source 300 draws air 101A' through connecting tube 148 to exhaust.

Atmospheric pressure sensor 124 provides absolute pressure or ambient air 101 entering the sensor 106. Output from sensors 120, 122, 124, are used to calculate parameters, as summarized in TABLE 1, thereby monitoring flow rate.

Figure 4:
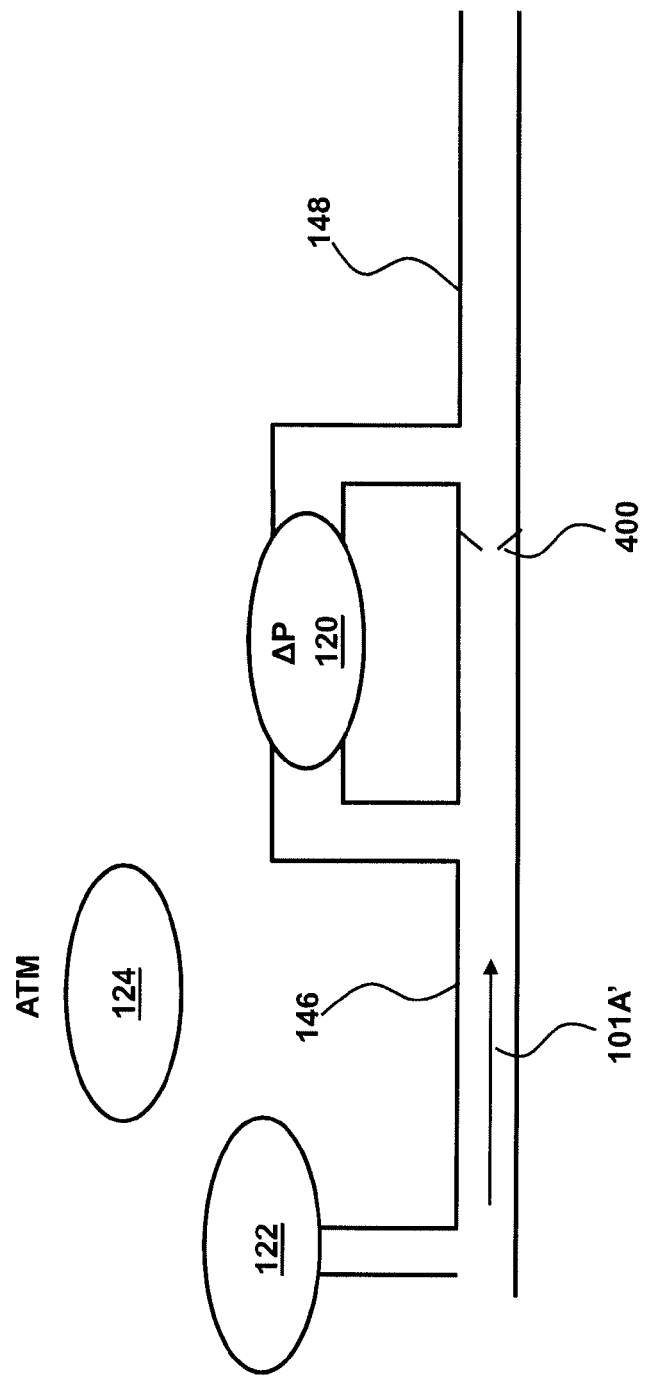
FIG. 4 illustrates the flow measurement orifice wherein pressure drop across an orifice is used to calculate flow rate based on the Bernoulli equation.

FIG. 4 illustrates the principles of pressure sensing within sensor 106 to monitor volumetric flow rate within sensor 106. The flow rate (molecules/second) or volumetric flow rate (volume of air/second) of air 101A' in sample tube 146 is calculated by differential pressure sensor 120 across restricting orifice 400. Pressure sensor 122 measures the density (e.g., pressure) of air inside the sensor 106. To attain the number of particulates at a desired volumetric flow, volumetric flow is determined by the flow rate and the atmospheric pressure as provided by differential pressure sensor 120 and pressure sensor 122, respectively. Pressure sensor 122 can be located elsewhere within sensor 106 (such as at optical block 200). Further details of the system is provided in U.S. Pat. No. 6,167,107.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a temperature range, a size or distance range, a time range, a velocity, a voltage, a pressure or rates thereof, a composition, or a concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

TABLE 1

FLOW MONITORING ALGORITHM

| Term | Description | Detail | Formula |
|---|---|---|---|
| $DPC_{offset}$ | Differential Pressure Sensor Offset Value | Measured at Calibration with no flow | |
| $DPC_{raw}$ | Differential Pressure Sensor Raw Value | Measured at Calibration with calibrated flow | |
| $DPC_{corrected}$ | Differential Pressure Sensor Corrected Value | Calculated at Calibration | $DPC_{raw} - DPC_{offset}$ |
| $DPI_{raw}$ | Differential Pressure Sensor Current Raw Reading (in-situ) | Measured in-situ | |
| $DPI_{corrected}$ | Differential Pressure Sensor Current Corrected Reading, | Calculated in-situ | $DPI_{raw} - DPC_{offset}$ |
| $APC_{raw}$ | Atmospheric Pressure Raw Value | Measured at Calibration with calibrated flow | |
| $APC_{corrected}$ | Atmospheric Pressure Corrected Value | Calculated at Calibration | $APC_{raw} + 0.285\ Vdc$ |
| $API_{raw}$ | Atmospheric Pressure Raw Value | Measured in-situ | |
| $API_{corrected}$ | Atmospheric Pressure Corrected Value | Calculated in-situ | $API_{raw} + 0.285\ Vdc$ |
| $BPC_{raw}$ | Bench Pressure Raw Value | Measured at Calibration with calibrated flow | |
| $BPC_{corrected}$ | Bench Pressure Corrected Value | Calculated at Calibration | $BPC_{raw} + 0.285\ Vdc$ |
| $BPI_{raw}$ | Bench Pressure Raw Value | Measured in-situ | |
| $BPI_{corrected}$ | Bench Pressure Corrected Value | Calculated in-situ | $BPI_{raw} + 0.285\ Vdc$ |
| $APR_{Calibration}$ | Absolute Pressure Ratio of $APC_{corrected}$ and $BPC_{corrected}$ | Calculated at Calibration with calibrated flow | $BPC_{corrected}/APC_{corrected}$ |
| $DPI_{target}$ | Calculated Differential Pressure Sensor Target Value | Calculated in-situ | $DPC_{corrected} * (BPI_{corrected}/BPC_{corrected})$ |
| Pass/Fail Criteria | Error range calculated for +/− 10% Δ Flow/Vacuum Induced Loss | Calculated in-situ | Flow Failure if: $DPI_{corrected} < 0.81 * DPI_{target}$<br>Flow Failure if: $DPI_{corrected} > 1.21 * DPI_{target}$ |
| $APR_{Insitu}$ | Absolute Pressure Ratio of $API_{corrected}$ and $BPI_{corrected}$ | Calculated in-situ | $BPI_{corrected}/API_{corrected}$ |
| Pass/Fail Criteria | Error range calculated for +/− 10% Δ Flow/Inlet Induced Loss | Calculated in-situ | Flow Failure if: $APR_{Insitu} < APR_{Calibration} * 0.9$<br>Flow Failure if: $APR_{Insitu} > APR_{Calibration} * 1.1$ |

I claim:

1. A method of monitoring flow rate of a gas in a particle sensor, said method comprising the steps of:
   providing a particle sensor comprising:
      a flow measurement orifice comprising a differential pressure sensor for measuring differential pressure across said flow measurement orifice;
      a critical orifice;
      a vacuum system for generating gas flow across said flow measurement orifice and said critical orifice;
   generating a flow of gas through said particle sensor by establishing a vacuum pressure at a position downstream of said critical orifice;
   determining a pressure drop (DPI) across said flow measurement orifice;
   determining atmospheric pressure (API);
   determining a pressure in said particle sensor (BPI) at a position that is upstream of said critical orifice;
   identifying a flow condition from said DPI, API and BPI values, wherein said flow condition is a flow rate error condition; and
   identifying said flow rate error condition as a vacuum-induced flow loss or an inlet-induced flow loss;
   thereby monitoring said flow rate in said particle sensor.

2. The method of claim 1, wherein said vacuum-induced flow loss is identified for:

$$DPI_{corr} < (1-\text{TOLERANCE})^2 * DPI_{target};\text{ or}$$

$$DPI_{corr} > (1+\text{TOLERANCE})^2 * DPI_{target};\text{ wherein:}$$

$DPI_{corr}$ is the differential pressure sensor current reading across said flow measurement orifice during particle sensor operation;

TOLERANCE is a user-selected flow rate tolerance level;
$DPI_{target}$ is a differential pressure sensor target value calculated as:

$$DPC_{corr} * (BPI_{corr}/BPC_{cor}),\text{ wherein:}$$

$DPC_{corr}$ is the differential pressure sensor value during system calibration;
$BPI_{corr}$ is the bench pressure value during particle sensor operation; and
$BPC_{corr}$ is the bench pressure value during system calibration.

3. The method of claim 2, wherein the TOLERANCE value is selected from a range that is greater than or equal to 5% and less than or equal to 15%.

4. The method of claim 3, wherein the TOLERANCE value is 10%.

5. The method of claim 1, wherein said inlet-induced flow loss is identified for:

$$APR_{insitu} < (1-\text{TOLERANCE})*APR_{calibration}; \text{ or}$$

$$APR_{insitu} > (1+\text{TOLERANCE})*APR_{calibration}; \text{ wherein}$$

$APR_{insitu}$ is the pressure ratio of $API_{corr}$ and $BPI_{corr}$ during particle sensor operation: $(BPI_{corr}/API_{corr})$, wherein:
 $API_{corr}$ is the atmospheric pressure value during particle sensor operation;
 $BPI_{corr}$ is the bench pressure value during particle sensor operation;
TOLERANCE is a user-selected flow rate tolerance level;
$APR_{calibration}$ is the pressure ratio of $APC_{corr}$ and $BPC_{corr}$: $(BPC_{corr}/APC_{corr})$, wherein:
 $BPC_{corr}$ is the bench pressure value at calibration; and
 $APC_{corr}$ is the atmospheric pressure at calibration.

6. The method of claim 5, wherein the TOLERANCE value is selected from a range that is greater than or equal to 5% and less than or equal to 15%.

7. The method of claim 6, wherein the TOLERANCE value is 10%.

8. The method of claim 1, wherein BPI is measured within an optical block of said particle sensor.

9. The method of claim 1, wherein said flow measurement orifice is positioned upstream of said critical orifice.

10. The method of claim 1, wherein the vacuum source is a house vacuum.

11. The method of claim 1, wherein the gas is air.

12. The method of claim 1, further comprising identifying a flow condition that deviates by 10% or more from a target flow rate.

13. The method of claim 12, wherein the target flow rate is 1 CFM.

14. The method of claim 12 further comprising identifying said flow rate error as related to a flow input obstruction or a loss in vacuum.

15. A method of monitoring volumetric flow rate of a gas in a particle sensor, said method comprising the steps of:
 providing a particle sensor comprising:
  a flow measurement orifice comprising a differential pressure sensor for measuring differential pressure across said flow measurement orifice, a critical orifice;
  a vacuum system for generating gas flow across said flow measurement orifice and said critical orifice;
 generating a flow of gas through said particle sensor by establishing a vacuum pressure at a position downstream of said critical orifice;
 determining a pressure drop (DPI) across said flow measurement orifice;
 determining atmospheric pressure (API); and
 determining a pressure in said particle sensor (BPI) at a position that is upstream of said critical orifice; and
 identifying a flow condition from said DP, AP and BP values, wherein said flow condition is identified as:
 a vacuum-induced flow loss for:

$$DPI_{corr} < (1-\text{TOLERANCE})^2*DPI_{target}; \text{ or}$$

$$DPI_{corr} > (1+\text{TOLERANCE})^2*DPI_{target}; \text{ wherein:}$$

$DPI_{corr}$ is the differential pressure sensor current reading across said flow measurement orifice during particle sensor operation;
 TOLERANCE is a user-selected flow rate tolerance level;

$DPI_{target}$ is a differential pressure sensor target value calculated as:

$$DPC_{corr}*(BPI_{corr}/BPC_{corr}), \text{ wherein:}$$

$DPC_{corr}$ is the differential pressure sensor value during system calibration;
 $BPI_{corr}$ is the bench pressure value during particle sensor operation; and
 $BPC_{corr}$ is the bench pressure value during system calibration;
or:
an inlet-induced flow loss for:

$$APR_{insitu} < (1-\text{TOLERANCE})*APR_{calibration}; \text{ or}$$

$$APR_{insitu} > (1+\text{TOLERANCE})*APR_{calibration}; \text{ wherein:}$$

$APR_{insitu}$ is the pressure ratio of $API_{corr}$ and $BPI_{corr}$ during particle sensor operation: $(BPI_{corr}/API_{corr})$;
 $API_{corr}$ is the atmospheric pressure value during particle sensor operation;
 $BPI_{corr}$ is the bench pressure value during particle sensor operation;
 TOLERANCE is a user-selected flow rate tolerance level;
 $APR_{calibration}$ is the pressure ratio of $APC_{corr}$ and $BPC_{corr}$: $(BPC_{corr}/APC_{corr})$, wherein:
 $BPC_{corr}$ is the bench pressure value at calibration; and
 $APC_{corr}$ is the atmospheric pressure at calibration;
thereby monitoring said volumetric flow rate in said particle sensor.

16. A particle sensor comprising:
 a particle counter;
 a flow measurement orifice comprising a differential pressure sensor for measuring differential pressure across said flow measurement orifice (DPI) during particle sensor operation;
 a critical flow orifice;
 a vacuum source for pulling ambient gas through each of said particle counter, flow measurement orifice and critical flow orifice;
 an atmospheric pressure sensor for measuring atmospheric pressure (API);
 a bench pressure sensor for measuring pressure in said particle sensor (BPI);
 a monitor operably connected to each of said differential pressure sensor, atmospheric pressure sensor and bench pressure sensor, wherein said monitor identifies a flow rate error from said DPI, API and BPI, wherein said flow rate error is identified as a vacuum-induced flow loss or an inlet-induced flow loss.

17. The particle sensor of claim 16, wherein said monitor is an alarm that indicates said flow-rate error.

18. The particle sensor of claim 16, wherein said flow-rate error is a 10% or greater deviation from a target flow rate of gas through said particle sensor.

19. The particle sensor of claim 16, wherein said flow rate error is for one or more conditions defined by:

$$DPI_{corr} < (1-\text{TOLERANCE})^2*DPI_{target};$$

$$DPI_{corr} > (1+\text{TOLERANCE})^2*DPI_{target};$$

$$APR_{insitu} < (1-\text{TOLERANCE})*APR_{calibration}; \text{ or}$$

$$APR_{insitu} > (1+\text{TOLERANCE})*APR_{calibration}; \text{ wherein:}$$

$DPI_{corr}$ is the differential pressure sensor current reading across said flow measurement orifice during particle sensor operation;
TOLERANCE is a user-selected flow rate tolerance level;

$DPI_{target}$ is a differential pressure sensor target value calculated as:

$$DPC_{corr}*(BPI_{corr}/BPC_{cor}), \text{ wherein:}$$

$DPC_{corr}$ is the differential pressure sensor value during system calibration;

$BPI_{corr}$ is the bench pressure value during particle sensor operation; and $BPC_{corr}$ is the bench pressure value during system calibration;

$APR_{insitu}$ is the pressure ratio of $API_{corr}$ and $BPI_{corr}$ during particle sensor operation: $(BPI_{corr}/API_{corr})$, wherein:

$API_{corr}$ is the atmospheric pressure value during particle sensor operation;

$BPI_{corr}$ is the bench pressure value during particle sensor operation;

$APR_{calibration}$ is the pressure ratio of $APC_{corr}$ and $BPC_{corr}$: $(BPC_{corr}/APC_{corr})$, wherein:

$APC_{corr}$ is the atmospheric pressure at calibration.

20. The particle sensor of claim 16, wherein said flow rate error condition is for a flow-rate that is greater than 10% deviation from a target flow-rate.

21. The particle sensor of claim 16 wherein the flow measurement orifice is positioned between said particle counter and critical flow orifice.

22. The particle sensor of claim 16, wherein the bench pressure sensor measures pressure within an optical block of said particle counter.

23. A particle sensor comprising:

a particle counter;

a flow measurement orifice comprising a differential pressure sensor for measuring differential pressure across said flow measurement orifice (DPI) during particle sensor operation;

a critical flow orifice;

a vacuum source for pulling ambient gas through each of said particle counter, flow measurement orifice and critical flow orifice;

an atmospheric pressure sensor for measuring atmospheric pressure (API);

a bench pressure sensor for measuring pressure in said particle sensor (BPI);

a monitor operably connected to each of said differential pressure sensor, atmospheric pressure sensor and bench pressure sensor, wherein said monitor identifies a flow condition from said DPI, API and BPI, and said flow condition is a flow rate error for one or more of:

$$DPI_{corr} < (1-\text{TOLERANCE})^2 * DPI_{target};$$

$$DPI_{corr} > (1+\text{TOLERANCE})^2 * DPI_{target};$$

$$APR_{insitu} < (1-\text{TOLERANCE}) * APR_{calibration}; \text{ and}$$

$$APR_{insitu} > (1+\text{TOLERANCE}) * APR_{calibration}; \text{ wherein:}$$

$DPI_{corr}$ is the differential pressure sensor current reading across said flow measurement orifice during particle sensor operation;

TOLERANCE is a user-selected flow rate tolerance level;

$DPI_{target}$ is a differential pressure sensor target value calculated as:

$$DPC_{corr}*(BPI_{corr}/BPC_{cor}), \text{ wherein:}$$

$DPC_{corr}$ is the differential pressure sensor value during system calibration;

$BPI_{corr}$ is the bench pressure value during particle sensor operation; and $BPC_{corr}$ is the bench pressure value during system calibration;

$APR_{insitu}$ is the pressure ratio of $API_{corr}$ and $BPI_{corr}$ during particle sensor operation: $(BPI_{corr}/API_{corr})$, wherein:

$API_{corr}$ is the atmospheric pressure value during particle sensor operation;

$BPI_{corr}$ is the bench pressure value during particle sensor operation;

$APR_{calibration}$ is the pressure ratio of $APC_{corr}$ and $BPC_{corr}$: $(BPC_{corr}/APC_{corr})$, wherein:

$APC_{corr}$ is the atmospheric pressure at calibration.

\* \* \* \* \*

UNITED STATES PATENT AND TRADEMARK OFFICE
CERTIFICATE OF CORRECTION

PATENT NO. : 8,800,383 B2  Page 1 of 1
APPLICATION NO. : 13/392057
DATED : August 12, 2014
INVENTOR(S) : Bates It is certified that error appears in the above-identified patent and that said Letters Patent is hereby corrected as shown below:

In the Specification

Column 2, line 60, replace "$DPC_{corr}/BP/_{corr}/BPC_{cor}$" with --$DPC_{corr}/BP/_{corr}/BPC_{corr}$--

Column 4, line 17, replace "$(BP/_{corr}/BPC_{cor})$" with --$(BP/_{corr}/BPC_{corr})$--

In the Claims

In claim 2, column 16, line 55, replace "$(BP/_{corr}/BPC_{cor})$" with --$(BP/_{corr}/BPC_{corr})$--

In claim 15, column 18, line 4, replace "$(BP/_{corr}/BPC_{cor})$" with --$(BP/_{corr}/BPC_{corr})$--

In claim 19, column 19, line 4, replace "$(BP/_{corr}/BPC_{cor})$" with --$(BP/_{corr}/BPC_{corr})$--

In claim 23, column 20, line 22, replace "$(BP/_{corr}/BPC_{cor})$" with --$(BP/_{corr}/BPC_{corr})$--

Signed and Sealed this
Sixth Day of January, 2015

Michelle K. Lee
*Deputy Director of the United States Patent and Trademark Office*